United States Patent [19]

Keenan et al.

[11] Patent Number: 4,956,357

[45] Date of Patent: Sep. 11, 1990

[54] BIOLOGICAL METHODS UTILIZING DIHYDROTESTOSTERONE HEPTANOATE

[76] Inventors: Bruce S. Keenan, 3639 Tartan, Houston, Tex. 77025; James T. Sparrow, 12119 Atwell, Houston, Tex. 77035

[21] Appl. No.: 842,346

[22] Filed: Mar. 28, 1986

[30] Foreign Application Priority Data

Mar. 30, 1984 [GB] United Kingdom ................. 8508404

[51] Int. Cl.$^5$ ............................................. A61K 31/56
[52] U.S. Cl. .................................................... 514/178
[58] Field of Search ...................... 260/397.4; 514/178

[56] References Cited
FOREIGN PATENT DOCUMENTS
7105486 of 0000 France .

OTHER PUBLICATIONS

Chemical Abstracts; vol. 75, (1971), #151981v; Wiechert et al.
Chemical Abstracts; vol. 76, (1972); #54602k; Mann et al.
Chemical Abstracts; vol. 88, (1978), #163945; Volovelskii et al.
JCE & M, C. Faiman et al., The Control of Gonadotropin Secretion in Complete Testicular Feminization, vol. 39, pp. 631–638.

*Primary Examiner*—Douglas W. Robinson
*Assistant Examiner*—Joseph A. Lipovsky
*Attorney, Agent, or Firm*—Fulbright & Jaworski

[57] ABSTRACT

Disclosed is synthesized dihydrotestosterone heptanoate, its method of synthesis, and its method of use as an androgenic hormone of male gynecomastia, as a hormonal probe, as well as other applications.

15 Claims, 4 Drawing Sheets

BIOLOGICAL METHODS UTILIZING DIHYDROTESTOSTERONE HEPTANOATE

FIELD OF THE INVENTION

The invention relates to dihydrotestosterone heptanoate, compositions including that compound, and methods of use thereof.

BACKGROUND OF THE INVENTION

Breast enlargement (gynecomastia) in adolescent males is a common phenomenon. Several methods of treatment have been tried. Treatment with the androgenic hormone testosterone has actually caused increased breast size (H. E. Carlson, *Gynecomastia*, 303 New Eng J. Med. 795-799 (1980)), Lrobably because testosterone is converted to the female sex hormone estradiol in vivo by the aromatase enzyme.

In another study, treatment was attempted with an alcoholic solution of Dihydrotestosterone (DHT) applied to the skin. J. M. Kuhn, R. Roca, M. H. Landot, M. Riev, J. P. Luton, Bricase, *Studies in the Treatment of Idiopathic Gynaecomastia With Percutaneous Dihydrotestosterone*, 520 Clinical Endocrinology 19:513 (1983). While in a majority of patients this was successful and systemic absorption: of DHT was indicated by elevations in its plasma levels, in about 1/5 of the subjects absorption was poor and there was no benefit. Also, in another ⅓ of the subjects, breast regression was incomplete. Another disadvantage of this technique is that the solution must be applied three to four times daily to be effective. This is inconvenient and esthetically objectionable.

It seems that for best results, the gonadotropins—Follicle Stimulating Hormone (FSH) and Leutinizing Hormone (LH)—should be suppressed, for they act on the testes to cause increased testosterone production which (as noted above) is believed to be converted to estradiol in those with gynecomastia. There is considerable dispute as to whether DHT causes suppression of LH or FSH, though suppression of LH alone has been noted in one study. R. J. Santen, *Is Aromatization of Testosterone to Estradiol Required for Inhibition of Luetinizing Hormone Secretion in Man?* 56 J. Clin. Invest. 1555. It seems otherwise clear, however, that long term suppression of LH or FSH can only be achieved through an inhibitor which itself remains in circulation for extended periods. Oral DHT is unsuitable as it is destroyed before reaching the circulatory system. If administered parenterally it has a very short half-life, and, as noted above, topical administration of solution is also effective only for a short time.

Dihydrotestosterone propionate has also been tried. C. Faiman, J. P. Winter, *The Control of Gonadotropin Secretion in Complete Testicular Feminization*, 39 J. Clin. Endocrinol. Metab. 631-637. However, it has only a one-to three day duration of action and was not effective in gonadotropin suppression. Id.

Insofar as insufficiency of androgenic hormones is treated the same way as gynecomastia—i.e., it is treated by an increase in systemic DHT levels—a thing effective in increasing systemic androgen levels should also function well to treat this syndrome. Moreover, a thing causing suppression of gonadotropins could be effective as a male contraceptive. LH suppression decreases intratesticular androgen levels due to decreased Leydig cell activity. This reduced cellular activity, especially in conjunction with FSH suppression, can significantly reduce or even terminate germ cell proliferation and sperm production. Although previous studies using esterified or unesterified DHT had failed to demonstrate FSH suppression, dihydrotestosterone heptanoate (DHT hep) would probably be suited for this use and all the others noted above.

SUMMARY OF THE INVENTION

Injection of dihydrotestosterone heptanoate, having the formula:

causes suppression of LH, FSH, testosterone and estradiol, and elevation of DHT levels. It is effective in doing so for about three weeks, and has also been shown effective in treatment of adolescent gynecomastia and hypogonadotrophic hypogonadism. The latter effect is due to the property of DHT-hep as a potent androgen. It causes enlargement of the male genitalia, growth of pubic hair, growth of facial hair, and increase in height and weight and acne.

DHT-hep, inasmuch as it suppresses LH and testicular testosterone production, could also be valuable as a hormonal probe. With its administration, LH from the anterior pituitary is suppressed and thus is not acting to cause testicular testosterone production. Demonstration of residual testosterone and estradiol in the blood after suppression of LH could therefore be used to determine the extent to which the adrenal gland produces testosterone and estradiol.

Because it suppresses gonadotropins, another promising use for this compound is as a male contraceptive.

Another potential use is as a test for androgen response, e.g., for detection in the newborn of male pseudohermaphoditism with androgen insensitivity. Early detection of insensitivity indicates that the infant should be assigned the female gender for feminization would necessarily occur at puberty.

DHT hep has an advantage over testosterone enanthate, the commonly used androgen preparation, in that it is not aromatized, and thus, gynecomastia is not a side effect. Since estrogens are considered to have an antagonistic effect on growth hormone action, growth in height with DHT therapy could theoretically be greater with DHT hep than with testosterone therapy.

Accordingly, it is an object of this invention to provide dihydrotestosterone heptanoate.

It is a further object of the invention to provide dihydrotestosterone heptanoate in substantially pure form.

It is further object of the invention to provide dihydrotestosterone heptanoate dissolved in a pharmaceutically acceptable adjuvant, such as sesame seed oil.

It is a further object of the invention to provide dihydrotestosterone heptanoate which, when administered to a patient, is broken down into dihydrotestosterone and heptanoic acid, the unesterified form of dihydrotestosterone binding to the human androgen receptor with high affinity, the heptanoate ester not binding tightly to the human estrogen receptor, and thus, dihydrotestosterone heptanoate acts through its conversion to dihydrotestosterone.

It is a further object of the invention to provide a method of treating hypogonadotrophism by internally administering dihydrotestosterone heptanoate.

A further object of the invention is a method of reducing the male sperm count by internally administering dihydrotestosterone heptanoate.

A further object of the invention is a method of treating for response to androgen by internally administering a dihydrotestosterone heptanoate and determining whether there is a suppression of leutinizing hormone.

A further object of the invention is a method of suppressing in vivo production of luetinizing hormone, follicle stimulating hormone, testosterone or estradiol hormone by internally administering dihydrotestosterone heptanoate.

A further object of the invention is the provision of a reaction product of dihydrotestosterone 5α-androstane-17β of 3-one), 4-dimethylaminopyridine, dichloromethane, and heptanoic anhydride useful in treating gynecomastia, hypoqonatrophism, as an androgen, a hormonal probe, reducing male sperm count, and useful for in vivo production of luetinizing hormone, follicle stimulating hormone, testosterone or estradiol.

A further object of the invention is a method of synthesizing dihydrotestosterone heptanoate.

A still further object of the invention is a method of preparing a pharmaceutical preparation comprising dihydrotestosterone heptanoate in a pharmaceutically acceptable adjuvant for administration to a male patient.

Other and further objects and advantages of the invention appear through the specification and claims.

BRIEF DESCRIPTION OF THE DRAWINGS

FIGS. 3A and 3B are graphs illustrating increases in plasma DHT one week after injection of 200 mg DHT-hep.

DESCRIPTION OF THE PRESENTLY PREFERRED EMBODIMENTS

The present invention is directed to the discovery that dihydrotestosterone heptanoate when injected in pharmacologically effective amounts into a male patient is effective in the treatment of adolescent gynecomastia and hydogonadotrophic hypogonadism, as a hormonal probe, as a male contraceptive, as a test for androgen response, for suppressing in vivo production of luetinizing hormone, follicle stimulating hormone, testosterone or estradiol. The dose or amount injected will vary with body size, weight, and purpose for which it is administered.

The dihydrotestosterone heptanoate is substantially pure. The starting material, dihydrotestosterone, contains a small amount (less than 1 percent) of androstanediols. The latter are naturally occurring human androgenic steroids and are esterified in the course of preparation. It is possible that some of the esterified androstanediols copurify with dihydrotestosterone heptanoate. Preferably it is dissolved in a pharmaceutically acceptable adjuvant, such as sesame seed oil, for injection, although other such adjuvants can be used such as cottonseed oil, corn oil, peanut oil and other refined fixed oils, and a variety of lycols, such as polyethylene glycol, propylene glycol and the like.

The invention is also directed to the preparation of dihydrotestosterone heptanoate (DHT-hep) and to the preparation of DHT-hep compounds for effective administration to patients.

In general, the method of synthesizing DHT-hep comprises adding to dihydrotestosterone in a suitable solvent dichloromethane, heptanoic anhydride and 4-dimethylaminopyridine. The mixture is stirred and stored until reacted. The reaction product is washed, then dried, and the solvent is removed leaving a colorless crystalline solid. Preferably the solid is recrystallized to remove impurities.

The solid is then further purified by dissolving in a suitable solvent and by preparative high pressure liquid chromatography. The solvent is removed, such as by evaporation, and DHT-hep is recrystallized.

To provide a suitable preparation for administration to a male patient, a pharmacologically effective amount is dissolved in a pharmaceutically acceptable adjuvant, such as sesame seed oil.

The following example is a presently preferred method of preparing or synthesizing DHT-hep, purifying it, and providing a solution containing it for injection into a male patient.

1. Example of Synthesizing DHT-hep

To 20.0 g (0.069 mol) dihydrotestosterone in 150 ml dichloromethane, 39 ml (36.4 g, 0.150 mol) of heptanoic anhydride was added, followed by addition of 3.0 g (0.025 mol) of 4-dimethylaminopyridine. A molar ratio of heptanoic anhydride:dihydrotestosterone of at least 2:1 is optimal. The amount of 4 dimethylpyridine may be varied depending upon the desired reaction rate (it is the catalyst). Dichloromethane is a Convenient solvent. The mixture was stirred at room temperature overnight (18 hrs.), and then washed three times each with 1N sodium hydroxide, 1N hydrochloric acid, and finally water. The dichloromethane layer was dried with anhydrous magnesium sulfate. The solvent was evaporated yielding a colorless crystalline solid which was recrystallized from acetone-water. The yield was 23.0 g (82%).

The DHT-hep was dissolved in hexane and purified by preparative high-pressure liquid chromatography, on a silica column equilibrated with hexane, and stepped to hexane ethyl acetate (9:1). After evaporating the solvent, the DHT-hep was recrystallized from acetone-water.

The compound had a melting point of 92.2°–94.4° C., and the structure was confirmed by infrared spectrophotometry, nuclear magnetic resonance spectroscopy, and gas chromatography mass spectroscopy.

2. Example of a Pharmaceutically-Acceptable Adjuvant

To prepare the DHT hep for administration, it was dissolved in sesame oil at 37° C. to a concentration of 190 mg/ml. (This was the limit of solubility of DHT-hep in sesame oil at 37° C. The warm sesame oil mixture was filtered in a laminar flow hood through a 0.20 micron filter into sterile injection vials. The vials were sealed, tested for sterility and pyroqens, and stored at room temperature.

3 Example of Treating Gynecomastia

Four pubertal boys, ages 14–16 years with gynecomastia which had lasted for more than 16 months and who all had breast diameters of more than 4 cm were studied. Their breast diameters ranged from 4.0 to 7.3 cm and breast areas from 13.5 to 41.4 cm$^2$ with mean breast area ($\pm$SEM) 24.3$\pm$4.1 cm$^2$.

The patients were given 200 mg DHT-hep in sesame oil intramuscularly. One week later plasma testosterone, DHT, LH, FSH, estradiol and prolactin were determined and 24-hour urinary LH and FSH were obtained. Subsequent testing was at 2, 3 and 4 weeks, and then just prior to each dose of DHT-hep. The second injection was given after four weeks but the frequency of injection was subsequently increased to every three weeks in three patients and every two weeks in one patient. In two boys, the dose of DHT-hep was increased to 400 mg. Treatment lasted 16 weeks. The patients were examined before each injection of DHT-hep and at two months and six months after therapy. Patients' unpaired, or when appropriate, paired tests were used to determine significant differences (p less than 0.05). Results were all expressed as mean$\pm$Standard Error.

a. Results

The results are illustrated in Table 1.

TABLE 1
CHARACTERISTICS OF STUDY PATIENTS

| Subject | M.S. | S.S. | J.D. | J.A. |
|---|---|---|---|---|
| Age (Yrs.) | 14 8/12 | 16 | 15 9/12 | 15 8/12 |
| Duration of Gynecomastia | 2 yrs | 16 mo. | 18 mo. | 18 mo. |
| Pubertal Stage (Tanner) | 4 | 4 | 4 | 4 |
| Treatment Frequency | every 3 wks | every 3 wks | every 2 wks | every 3 wks |
| Dose | 200 mg | 400 mg | 200 mg | 400 mg |
| BEFORE TREATMENT | | | | |
| Breast Diameter (cm) | 4.0 | 7.3 | 4.8 | 5.6 |
| Breast Area (cm$^2$) | 13.5 | 41.4 | 17.7 | 24.6 |
| Testosterone (ng/dl) | 517 | 174 | 317 | 129 |
| Estradiol (pg/ml) | 30 | 21 | 28 | 16 |
| FSH (ng/ml) | 334 | 157 | 175 | 96 |
| LH (ng/ml) | 25 | 15 | less than 11 | less than 11 |
| DHT (ng/dl) | 48 | 27 | 50 | 43 |
| 16 WKS TREATMENT | | | | |
| Breast Diameter (cm) | 2.3 | 4.2 | 2.3 | 2.7 |
| Breast Area (cm$^2$) | 4.0 | 13.9 | 4.0 | 6.1 |
| % Decrease in Breast Area | 70.1 | 66.6 | 77.5 | 75.2 |
| Testosterone (ng/dl) | 40 | 36 | 34 | less than 25 |
| Estradiol (pg/ml) | less than 10 | 16 | 15 | less than 10 |
| FSH (ng/ml) | less than 27 | 39 | 61 | 34 |
| LH (ng/ml) | less than 11 | less than 11 | less than 11 | less than 11 |
| DHT (ng/dl) | 171 | 313 | 292 | 336 |
| 2 MO. POST TREATMENT | | | | |
| Breast Diameter (cm) | 2.3 | 3.3 | 2.3 | 2.6 |
| Breast Area (cm$^2$) | 4.0 | 12.6 | 4.0 | 6.0 |
| % Decrease in Breast Area | 70.1 | 69.9 | 77.5 | 75.5 |
| Testosterone (ng/dl) | 297 | 140 | 244 | 178 |
| Estradiol (pg/ml) | 22 | 23 | 18 | 12 |
| FSH (ng/ml) | 150 | 143 | 120 | 73 |
| LH/ng/ml) | 14 | 19 | 27 | less than 11 |
| DHT (ng/dl) | 40 | 160.8 | 82 | 88 |

As seen from Table 1, all the patients experienced a significant decrease in breast size to a mean breast area of 7.0$\pm$1.5 cm$^2$ (p less than 0.002) after 16 weeks of treatment. The decrease in breast area ranged 66.6 to 77.5 percent. No regrowth of breast tissue occurred in any subject when they were seen at two and six months after therapy was discontinued. One patient (MS) has been followed for nine months with no increase in breast size.

Figure 1:
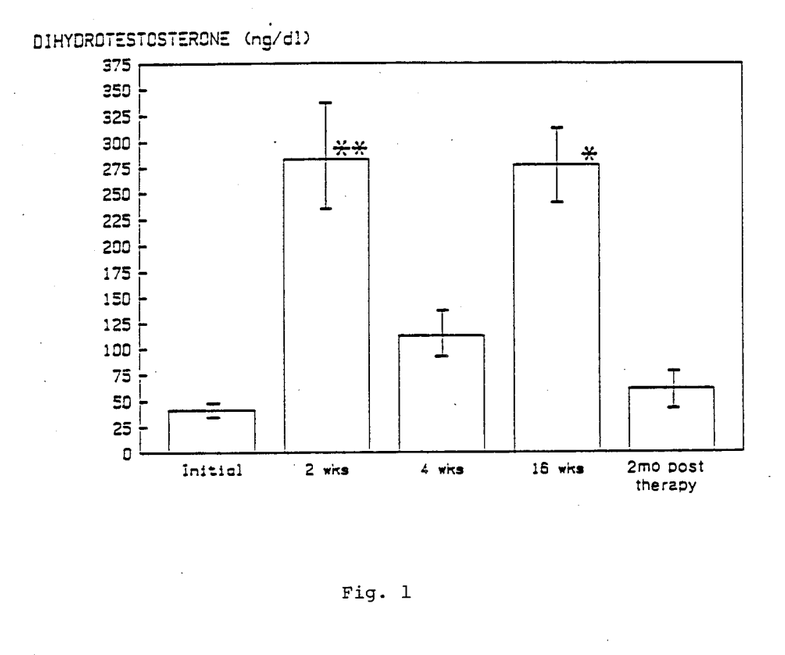
FIG. 1 is a graph illustrating the effect of the injection of dihydrotestosterone heptanoate on plasma DHT.

Mean plasma DHT concentration before treatment was 42.1$\pm$5.1 ng/dl. As seen in FIG. 1, Plasma DHT concentration rose in response to the initial injection of DHT-hep to 283.6$\pm$51.3 ng/dl at two weeks, then fell to 112.8$\pm$21.2 ng/dl at four weeks. With increased frequency of injections, mean pre-injection plasma DHT remained elevated throughout the treatment period measuring 278.2$\pm$36.9 ng/dl at 16 weeks, three weeks after the last injection. Two months after therapy the DHT had decreased to 61.3$\pm$14.7 ng/dl.

Figure 2A:
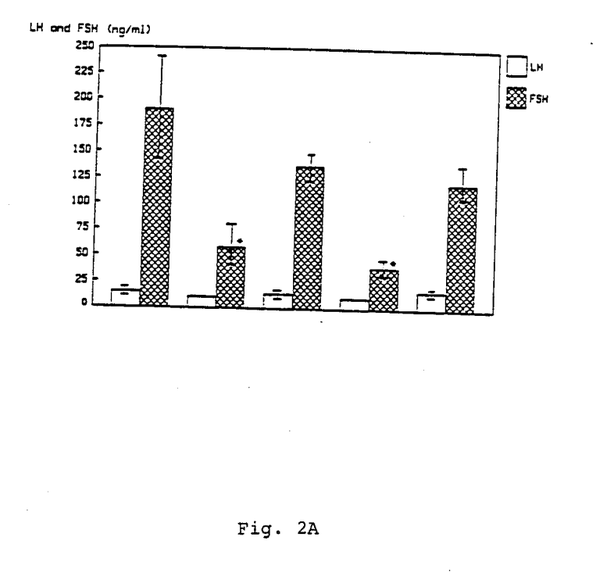
FIGS. 2A and 2B are graphs illustrating significant decreases in plasma FSH, testosterone and estradiol.

Administration of dihydrotestosterone heptanoate caused suppress-ion of the pituitary-testicular axis. Thus, in response to elevated DHT levels in plasma, there were statistically significant decreases in plasma FSH, testosterone and estradiol, monitored by using patients unpaired or paired as shown in FIGS. 2(A) and 2(B).

The plasma LH was low before treatment in three of the patients so that further suppression of LH was not statistically significant. Mean FSH decreased from 190.5$\pm$50.7 ng/ml before treatment, to 58.8$\pm$18.5 ng/ml at two weeks, and 40.3$\pm$7.3 ng/ml at 16 weeks, as shown in FIG. 3A.

Figure 2B:
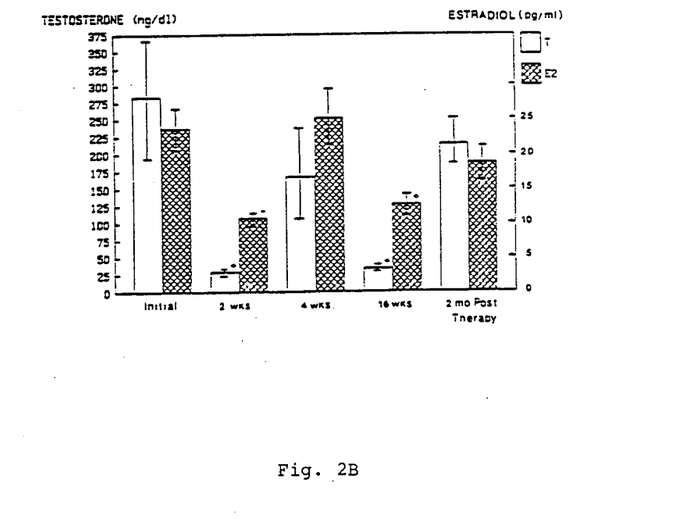

Mean plasma testosterone level decreased from 283.8$\pm$87.5 ng/dl before therapy, to 29.5$\pm$3.3 ng/dl at two weeks and was 33.8$\pm$3.2 ng/dl at 16 weeks, as shown in FIG. 2B.

The mean estradiol level decreased from 23.8$\pm$3.2 pg/ml to 10.8$\pm$0.8 pg/ml at two weeks and was 12.8$\pm$1.6 pg/ml by 16 weeks. Twenty-four hour urinary LH and FSH were both decreased one week after injection. Before treatment mean urinary LH was 13.0$\pm$1.3 IU/day and FSH 8.4$\pm$0.8 IU/day. After 1 week of treatment urinary LH was 7.4$\pm$3 and FSH 2.9$\pm$0.1. Two months after therapy plasma FSH had risen to 121.5$\pm$17.4 ng/ml, testosterone increased to 214.9$\pm$34.8 ng/dl and estradiol to 18.8$\pm$2.5 pg/ml.

Figure 3A:
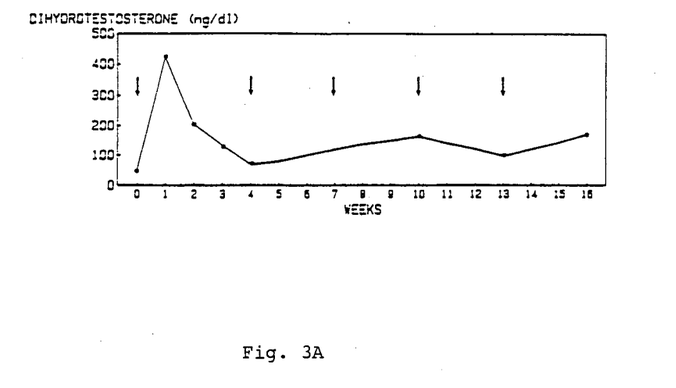

As illustrated in FIGS. 3A and 3B, there was a 5–8 fold increase in plasma DHT one week after injection of 200 mg DHT-hep.

Figure 4:
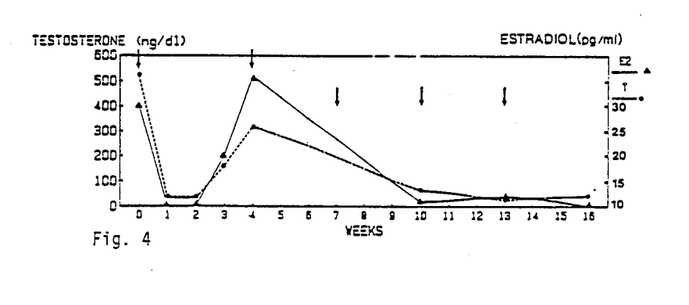
FIGS. 4A and 4B are graphs similar to FIGS. 3A and 3B in which the dose was increased to 400 mg.
Figure 4A:
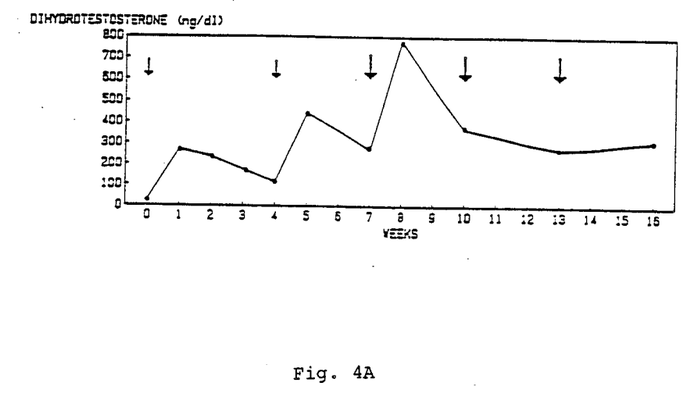
Figure 4B:
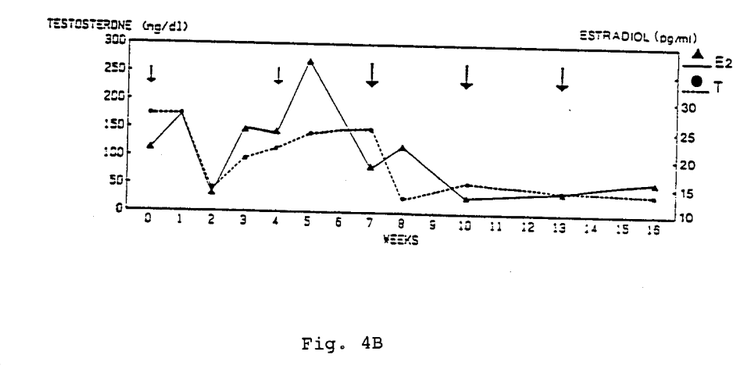

The elevated DHT level was accompanied by reductions in testosterone and estradiol. In all subjects maximal suppression of testosterone and estradiol occurred at two weeks post injection followed by rebound to pretreatment levels by four weeks. Suppression of testosterone and estradiol was maintained by giving the injections every two to three weeks. In two subjects (SS & JA) estradiol was not adequately suppressed at the 200 mg dose of DHT-hep; so the dose was increased to 400 mg (FIGS. 4A and 4B).

In another set of tests results not shown) 10 adolescent patients were treated with DHT-hep, and all showed plasma concentrations of 300–800 ng/dl—near the level in normal adult males. All showed significant reduction in breast size, accompanied by reduction of plasma concentrations of LH, FSH, testosterone and estradiol.

Thus, intramuscular injections of DHT-hep resulted in regression of breast tissue in all four adolescent boys studied. Although spontaneous disappearance of mild breast enlargement during adolescence occurs in the majority of boys, spontaneous regression was very unlikely in these patients since the breast diameters were greater than 4 cm and gynecomastia had been present more than 16 months without any indication of regression. The degree of breast reduction was cosmetically acceptable to the boys, and there was no regrowth of breast tissue six to nine months after therapy was discontinued, although the hormone levels had returned to near pre-treatment values.

Based on the results of binding affinity studies of DHT and DHT-hep binding to estrogen receptor and androgen-receptor (results not shown), it is hypothesized that DHT (produced by hydrolysis of DHT hep) acts on androgenic pathways rather than through an estrogen mechanism in suppression of gonadotropins. It is also believed that an androgen-action, rather than an estrogen action, acts to prevent breast enlargement.

It seems that the DHT hep preparation delivers androgen in DHT form, which results in continuous blood levels of DHT and suppression of estradiol.

4. Example of Using DHT-hep as an Androgen

DHT-hep was given to two patients for the purpose of stimulating development of the male external genitalia. One was a 26 year old man with hypogonadotrophic hypogonadism. In that patient pretreatment plasma testosterone and dihydrotestosterone concentrations were very low (less than 15 ng/dl). Administration of DHT-hep, 200 mg/month, intramuscularly over 6 months resulted in an increase in penile length from 4 cm to 8 cm and of penile diameter from 1.5 to 2.5 cm. Pubic hair increased and erections and ejaculations were reported by the patient. There was also a significant increase in muscle mass. The second patient was a boy in early puberty with qynecomastia. During treatment with DHT-hep over 4 months penile length increased significantly despite the fact that plasma testosterone and LH were suppressed. Also, pubic and auxiliary hair increased, and there was a 3 5 kg. weight gain. Thus the increase in secondary sexual development is attributable to the androgenic action of DHT

5. Example of Using DHT-hep as a Hormonal Probe

Insofar as it seems that DHT-hep suppresses LH and FSH (which are produced by the pituitary gland and act on the testes), it could be used to determine the relative contribution of the testes and adrenal gland as sources of testosterone and estradiol. In fact, in two of the four boys tested (see above), significant estradiol levels persisted even where LH and testosterone were suppressed. This indicates the adrenal is possibly manufacturing precursors of estradiol which ultimately cause some forms of gynecomastia.

While presently preferred embodiments of the invention have been given for purposes of disclosure, changes and modifications and other applications thereof may be made which are within the spirit of the invention as defined by the scope of the claims set forth below.

I claim:

1. A method of treating gynecomastia comprising, internally administering to a male patient a pharmacologically effective amount of dihydrotestosterone heptanoate.

2. The method of claim 1 wherein, the dihydrotestosterone heptanoate is administered dissolved in a pharmaceutically acceptable adjuvant.

3. The method of claim 2 wherein, the composition is injected intramuscularly.

4. The method of claim 1 wherein, the dihydrotesterone heptanoate is administered dissolved in sesame seed oil.

5. The method of claim 4 wherein, from about 200 mg to 400 mg of dihydrotestosterone heptanoate is administered every three weeks.

6. A method of treating hypogonadotrophism comprising, internally administering to a male patient a pharmacologically effective amount of dihydrotestosterone heptanoate.

7. The method of claim 6 wherein, the dihydrotestosterone heptanoate is dissolved in pharmaceutically acceptable adjuvant.

8. The method of claim 6 wherein, the dihydrotestosterone heptanoate is dissolved in sesame seed oil.

9. The method of claim 6 wherein, the composition is injected intramuscularly.

10. The method of claim 6 wherein, from about 200 mg to 400 mg of dihydrotestosterone heptanoate is administered every three weeks.

11. A method of testing for response to androgens comprising, internally administering to a male patient a pharmacologically effective amount of dihydrotestosterone heptanoate, and measuring the size of the genitalia and suppression of luetinizing hormone as a result thereof.

12. The method of claim 11 wherein, the dihydrotestosterone heptanoate is administered dissolved in a pharmaceutically acceptable adjuvant.

13. A method of suppressing in vivo production of hormone, follicle stimulating hormone, testosterone or estradiol comprising, internally administering to a male patient a pharmacologically effective amount of dihydrotestosterone heptanoate 14. The method of claim 13 wherein, the dihydrotestosterone heptanoate is administered dissolved in a pharmaceutically acceptable adjuvant.

15. The method of claim 14 wherein the dihydrotestosterone heptanoate is administered dissolved in sesame seed oil.

* * * * *

UNITED STATES PATENT OFFICE
CERTIFICATE OF CORRECTION

Patent No. 4,956,357    Dated September 11, 1990

Inventor(s) Bruce S. Keenan, James T. Sparrow

It is certified that error appears in the above-identified patent and that said Letters Patent is hereby corrected as shown below:

Column 1, line 16, change "I.robably" to -- probably --

Column 1, line 22, after "Luton," add -- H. --

Column 1, line 26, after "absorption" delete -- : --

Column 1, line 57, change "one-to three" to -- one-to-three --

Column 3, line 21, before "5α-androstane-" add -- ( --

Column 3, line 24, change "hypoqonatrophism" to -- hypogonatrophism --

Column 3, line 56, change "hydogonadotrophic" to -- hypogonadotrophic --

Column 4, line 6, change "lycols" to -- glycols --

Column 4, line 51, after "chromatography" delete -- , --

Column 4, line 66, after "C." add -- ) --

Column 6, line 28, change "suppress-ion" to -- suppression --

Column 6, line 67, before "results" add -- ( --

Column 7, line 45, change "qynecomastia to -- gynecomastia --

Column 7, line 49, change "3 5 kg." to -- 3.5 kg. --

Column 7, line 51, after "DHT" add -- . --

UNITED STATES PATENT AND TRADEMARK OFFICE
CERTIFICATE OF CORRECTION

PATENT NO. : 4,956,357

DATED : September 11, 1990

INVENTOR(S) : Bruce S. Keenan, James T. Sparrow

It is certified that error appears in the above-identified patent and that said Letters Patent is hereby corrected as shown below:

Column 8, line 50, after "production of" add -- leutinizing --

Signed and Sealed this

Seventh Day of January, 1992

Attest:

HARRY F. MANBECK, JR.

*Attesting Officer*                    *Commissioner of Patents and Trademarks*